United States Patent
Groisman et al.

(10) Patent No.: US 7,892,836 B2
(45) Date of Patent: Feb. 22, 2011

(54) PNEUMATIC CAPILLARY GUN FOR BALLISTIC DELIVERY OF MICROSCOPIC PARTICLES INTO TISSUE

(75) Inventors: Alexander Groisman, San Diego, CA (US); Claire Simonnet, San Diego, CA (US); Dmitry Rinberg, Princeton, NJ (US)

(73) Assignee: The Regents of the University of California, Oakland, CA (US)

( * ) Notice: Subject to any disclaimer, the term of this patent is extended or adjusted under 35 U.S.C. 154(b) by 681 days.

(21) Appl. No.: 11/815,765

(22) PCT Filed: Feb. 13, 2006

(86) PCT No.: PCT/US2006/005151

§ 371 (c)(1),
(2), (4) Date: Aug. 7, 2007

(87) PCT Pub. No.: WO2006/086782

PCT Pub. Date: Aug. 17, 2006

(65) Prior Publication Data

US 2008/0206870 A1    Aug. 28, 2008

Related U.S. Application Data

(60) Provisional application No. 60/593,775, filed on Feb. 11, 2005.

(51) Int. Cl.
  *C12N 15/87*    (2006.01)
(52) U.S. Cl. .................... 435/459; 435/285.3; 435/470
(58) Field of Classification Search ........................ None
  See application file for complete search history.

(56) References Cited

U.S. PATENT DOCUMENTS

| 5,525,510 | A | 6/1996 | McCabe et al. |
| 5,584,807 | A | 12/1996 | McCabe |
| 5,853,663 | A | 12/1998 | Wittig et al. |
| 5,947,928 | A | 9/1999 | Muller |
| 6,232,113 | B1 | 5/2001 | Lee |
| 2003/0168592 | A1* | 9/2003 | Yamada et al. .............. 250/288 |

OTHER PUBLICATIONS

Rinberg et al., "Pneumatic Capillary Gun for Ballistic Delivery of Microparticles", Applied Physics Letters 87, 014103, pp. 1-3 (2005).
"Inside the Gene Gun", Inventing Tomorrow (Fall 2000).

* cited by examiner

*Primary Examiner*—James S Ketter
(74) *Attorney, Agent, or Firm*—Eleanor M. Musick; Procopio, Cory, Hargreaves & Savitch, LLP

(57) ABSTRACT

The capillary gun for delivery of ballistic particles to a target includes an inner capillary tube disposed concentrically within an outer capillary tube with the input end of the inner tube connected to a channel through which a continuous flow of high speed helium gas carrying ballistic particles is introduced. The outer capillary tube, which is connected to a vacuum source, has an outlet end that extends slightly beyond the end of the inner tube. A cap placed over the output end of the outer tube has an opening at its center through which the particles exit the device. The vacuum source applies continuous suction to the space between the outer tube and the inner tube, drawing the gas from the output end of the inner tube while the inertia of the accelerated particles causes them to continue in the axial direction through the exit opening for delivery to the target. Multiple particle injectors provide for the concurrent injection of different materials without disruption of the gas flow.

33 Claims, 7 Drawing Sheets

Figure 1A:
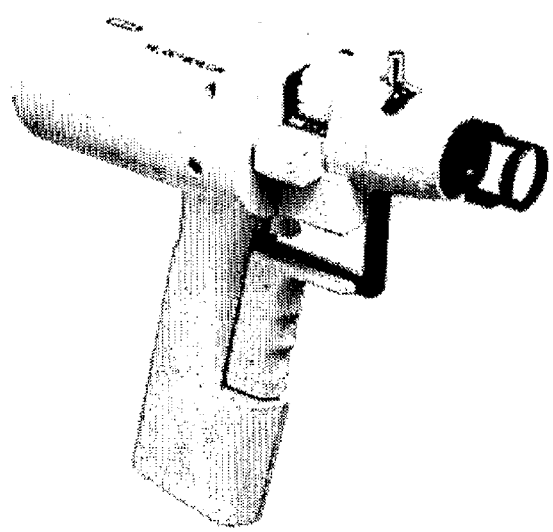

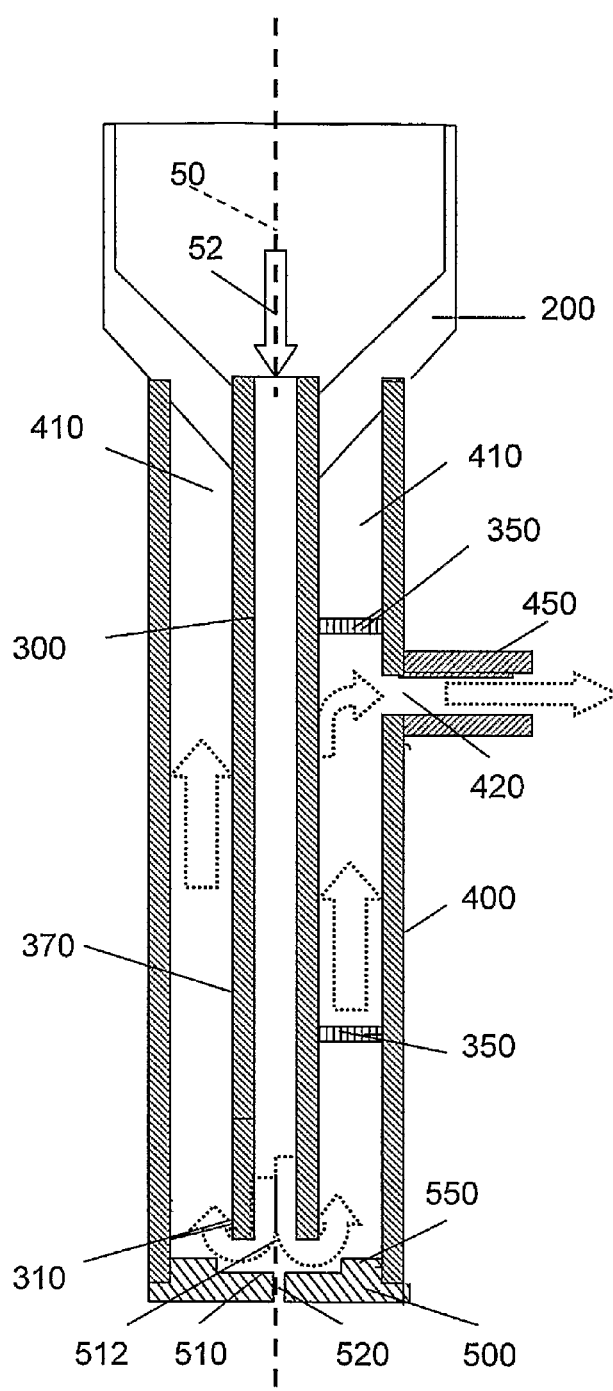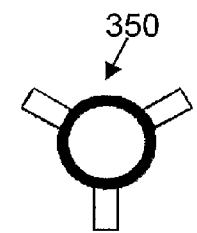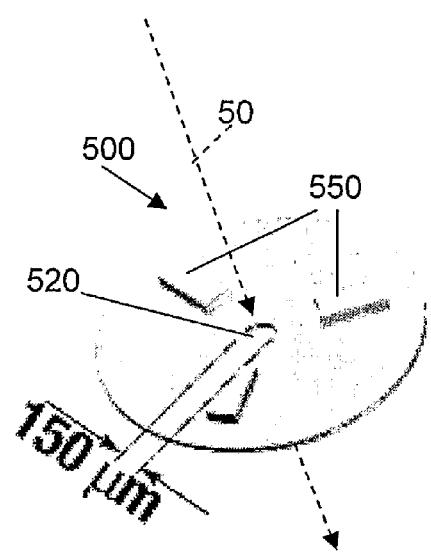
Fig. 3c
Fig. 3a
Fig. 3b

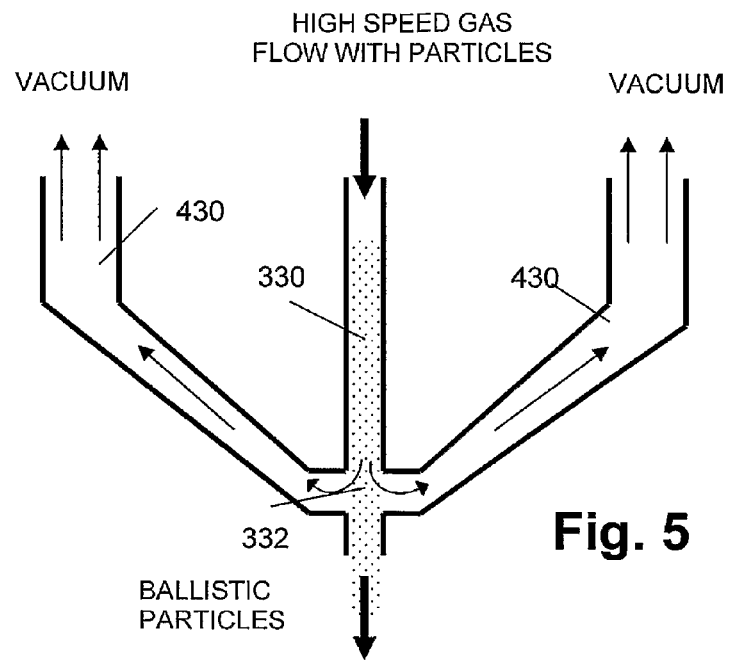
Fig. 5
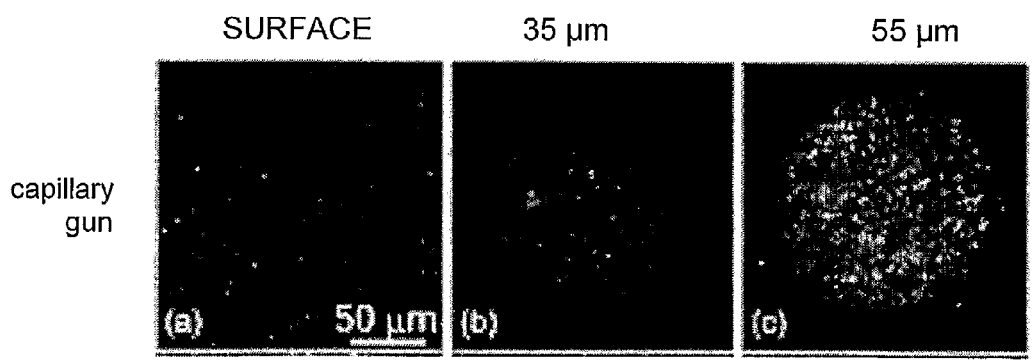
Fig. 6a  Fig. 6b  Fig. 6c
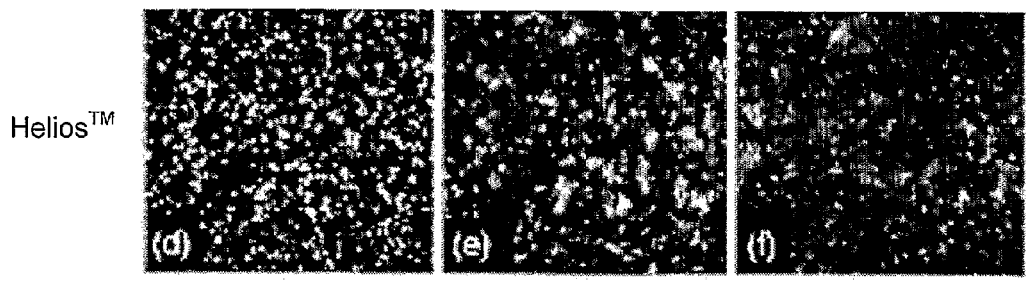
Fig. 6d  Fig. 6e  Fig. 6f

PNEUMATIC CAPILLARY GUN FOR BALLISTIC DELIVERY OF MICROSCOPIC PARTICLES INTO TISSUE

RELATED APPLICATIONS

This application claims the benefit of priority of U.S. Provisional Application Ser. No. 60/593,775, filed Feb. 11, 2005, which is incorporated herein by reference in its entirety.

GOVERNMENT RIGHTS

Pursuant to 35 U.S.C. §202(c), it is hereby acknowledged that the U.S. Government has certain rights in the invention described herein, which was made in part with funds from The National Institutes of Health, Grant No. R01MH056090.

FIELD OF THE INVENTION

The invention relates generally to in situ modification of genes and modulation of gene expression in tissue and more particularly to an instrument and method for insertion of foreign chemical or genetic material into soft targets such as tissue with minimal cell damage.

BACKGROUND OF THE INVENTION

Modulating gene expression by transfection or RNA-interference (RNAi) is a powerful means for studying the functions of genes. Realization of both techniques depends on delivery of the corresponding nucleic acids into cells in a tissue. The existing methods for localized delivery, e.g. microcapillary injection and electroporation, are laborious, invasive and often damaging.

Several techniques for introducing nucleic acids into cells and tissues are currently in use, including viral transformation, lipofection, electroporation, direct injection through microcapillaries and ballistic carrier particle delivery. In the latter technique, termed "biolistic", the molecules to be delivered are carried by micron-size particles of a heavy metal that are accelerated to high speeds and launched into the target cells. Substances injected into cells using the biolistic method have included DNA, fluorescent dyes, and RNA. The particle-mediated delivery is not sensitive to permeability of the cell membrane to particular reagents and lacks the potentially deleterious effects of viruses and lipofection. It can also be particularly advantageous for live tissue applications, because it does not depend on molecular diffusion within tissue and can target cells in internal layers. Nevertheless, the application area of the particle -mediated delivery has been limited by the current design of "gene guns" used for particle acceleration.

Gene gun operation can be based on a variety of different principles. In one method, a shock wave can be generated by a chemical explosion (dry gunpowder), a discharge of helium gas under high pressure, by vaporization of a drop of water through a electric discharge at high voltage and low capacitance, or at low voltage and high capacitance. Most of the original work on this technique is described in patents by inventors from Cornell University and Agracetus, Inc. of Middleton, Wis. Another technique is detailed in U.S. Pat. No. 5,525,510, incorporated herein by reference, and falls in the class of "fluid effects" for achieving high power with little damage to the tissue. This patent describes a gene gun using the "Coanda Effect" to accelerate the projectiles. The Coanda Effect is a passive design using the geometry of the diverter of the gas stream to pull the accelerant away from the nozzle by having it follow a curved surface.

Figure 1B:
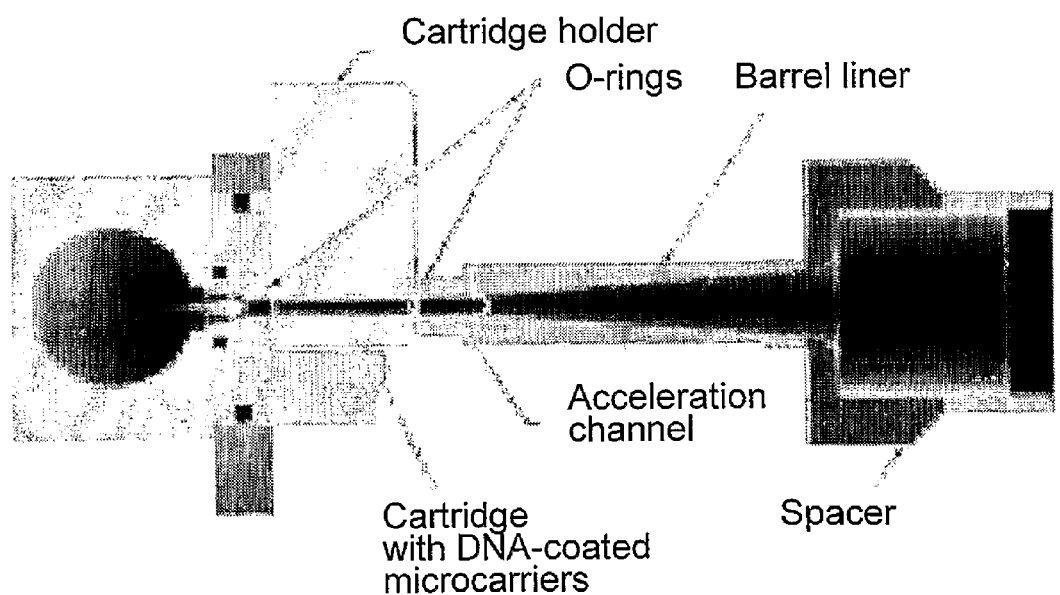

Existing gene guns, including the table-top PDS-1000 and the popular hand-held Helios (both available from Bio-Rad Laboratories of Hercules, Calif.), deliver particles to relatively large areas ($cm^2$) with limited accuracy and reproducibility. In addition, the tissue targeted by a Helios™ gun may be damaged by the jet of gas emerging from the gun nozzle. An image of the Helios™ gun and a diagram showing the basic components of the device are provided in FIGS. 1a and 1b, respectively. Beads coated with genetic material are glued to the internal wall of the cartridge using a preparation available from the manufacturer. The gene gun uses compressed helium at pressures of 7-20 atm. Particles are accelerated by helium flow in the "acceleration channel", which is followed by an opening cone, "barrel liner", and a spacer, illustrated in FIG. 1b. The two latter elements are intended to vent the helium gas away from the target to minimize cell surface impact. Nonetheless, unlike the narrow holes perforated by the micron size particles, the impact of the high speed helium jet emerging from the barrel may inflict significant damage to the tissue located in front of the barrel. Therefore, the problem of stopping/diverting the flow of the gas accelerating the particles has been a major concern with the gene gun design.

With current methods, there is a trade off between penetration depth and tissue damage. The Helios™ device is limited in that the range of bead penetration into the tissue is less than ~50 μm. To increase the penetration depth, the particles must be accelerated to a higher velocity, which can only be achieved by increasing the helium jet pulse velocity which, in turn, increases damage to the tissue.

Both in-vivo and in slice preparation would greatly benefit from a method for delivery of dyes or genetic material into the cells that lie as deep as 200-400 μm. A technique for delivery fluorescent dyes into living tissue is described by Gan, W. B., J. Grutzendler, et al. (2000), "Multicolor "DiOlistic" Labeling of the Nervous System using Lipophilic Dye Combinations," *Neuron* 27(2): 219-25. A Bio-Rad gene gun was used to deliver multiple fluorescent dyes into neuronal tissue for anatomical study. The described method had limited effect, however, due to the low penetration depth of the beads. Efforts to reduce damage caused by the gas flow have led to deceleration of the particles and a resulting reduction of their penetration depth. This limits the usefulness the current technology for applications in mammalian brain tissue, where most of the cell bodies lie 100 μm or more below the surface.

Tests using an agarose gel to emulate brain tissue showed that it is possible to obtain a major increase in the depth of penetration with a more focused jet of helium, however, there was a concomitant increase in damage to the gel surface. Accordingly, the need remains for a gene gun that can reproducibly achieve large penetration depths with minimal damage. Moreover, there is demand for new techniques of localized, accurate, reproducible and non-damaging delivery of substances such as nucleic acids and dyes into live tissue. The present invention is directed to such a device and method.

BRIEF SUMMARY OF THE INVENTION

It is an object of the present invention to provide a pneumatic capillary gun for localized ballistic delivery of microparticles deep into live tissues with high reproducibility and good control of location and size of the targeted region, while minimizing the damage resulting from the delivery method.

According to the present invention, particles are accelerated to high speeds by a flow of compressed gas such as helium, as in the prior art gene gun. However, in the inventive device, a vacuum suction is incorporated near the outlet of the gun to divert substantially all of the gas flow without perturbing the motion of the particles. Thus, damage to the tissue by the powerful jet of the gas is avoided. In further contrast to the prior art gene gun, the flow of helium in the inventive device can be made continuous rather than pulsatile, and launching of particles into the target is implemented by their injection into the continuous flow with a minimal perturbation to the speed of the flow. By using particles with different coatings stored in separate reservoirs and independently injected into the helium flow, different combinations of substances, e.g. nucleic acids and fluorescent dyes, can be concurrently delivered to specified regions of a tissue with a single capillary gun.

In an exemplary embodiment, a capillary tube is disposed concentrically within an a vacuum tube with the input end of the inner tube connected to a tubing line through which high speed helium gas is introduced. The vacuum tube, which is connected to a vacuum source, has an output end that extends slightly beyond the end of the inner tube. A cap placed over the output end of the outer tube has an opening at its center through which the particles exit the device. The vacuum source applies continuous suction to the space between the outer tube and the inner tube, drawing the helium from the output end of the inner tube while the inertia of the accelerated particles causes them to continue in the axial direction through the cap opening toward the target. The spacing between the outlet ends of the inner tube and the outer tube is selected to achieve the desired deflection of gas flow without interfering with the velocity or forward trajectory of the particles. In the exemplary embodiment, the spacing is on the order of 1 mm or less.

The use of a vacuum to divert the gas flow has multiple advantages over the solution attempted in the prior art gene gun. First, unless particles of excessively large size or at excessively high number are used, the inventive device inflicts no mechanical damage to even the softest live tissues. The unavoidable perforation from the micro-particle tracks can normally be quickly healed by the affected cells. Second, the acceleration of the particles is more uniform, and assuming a narrow distribution of their sizes, the particles have similar velocities when emerging from the gun, and their penetration depths into the tissue are uniform and reproducible. Third, the targeted area is defined by the size of the opening in the cap, which is generally small and variable, allowing for highly localized and accurately aimed particle delivery.

The inventive device gives the technique of particle-mediated (biolistic) delivery a new capability: to inject substances, change gene expression and perform staining in a microscopic region of a tissue, confined in three dimensions and targeted with high precision, without damage to the tissue. In one embodiment, the device is combined with optical targeting means, a light source, such a laser, with a focusing lens. The inventive device is low cost, requires low gas pressures, is easy to manage and, thus, has more versatile applications than the prior art devices.

The inventive device can launch particles of different shapes, including spherical beads and short thin wires that be used as microelectrodes. The length of the gun can be varied and the outside diameter of the gun can be about 1 mm or smaller. This variability permits the dimensions of the gun to be optimized for insertion into small openings and target tissues below the body surface to deliver genetic material or fluorescent dyes to the tissues. The small size of the device makes it ideal for insertion into small surgical incisions. As an example, it can be used in ophthalmology for gene or drug treatment of retinal cells. In combination with endoscope the inventive device can be used for targeting tissue of internal organs. Other applications include localized transdermal drug delivery.

By using particles with different coatings stored in separate reservoirs and independently injected into the gas flow in the gun, different sets of nucleic acids, dyes and other substances can be delivered into specified regions of a tissue, embryo, organ, animal, plant or a cell culture on a substrate, leading to expression or inhibition of different combinations of genes, or staining with different combinations of dyes. The gun can also be mounted on a motorized support for programmed motion and positioning in 3D, allowing a pre-designed spatial pattern of combinations of DNA, RNA, dyes or other substances to be inscribed into the biological specimen (a tissue, a cell culture on a substrate etc.) by shooting different sets of particles into its different regions. This will allow concurrent manipulation of expression of multiple genes (or of multiple aspects of cell/tissue physiology in general) according to the pre-designed spatial pattern in the targeted specimen. To increase the throughput, the individual capillary guns can be combined into linear (or two-dimensional) arrays, similar to multi-channel pipetters used with multi-well plates, with common supply of pressurized gas (He) and vacuum, and with common or individually controlled particle injection.

BRIEF DESCRIPTION OF THE DRAWINGS

FIG. 1*a* is a perspective view of a prior art gene gun.

FIG. 1*b* is a schematic showing the key components of the prior art gene gun.

FIG. 2 is a diagrammatic side view of the inventive capillary gun;

FIGS. 3*a*-3*c* illustrate details of the barrel of the capillary gun, where FIG. 3*a* is a cross-sectional view of the barrel of the capillary gun taken along line B-B of FIG. 2; FIG. 3*b* is a perspective view of the end cap; and FIG. 3*c* is a top view of a centering piece.

FIG. 4 is a schematic drawing illustrating the gas and flow patterns in the barrel of the capillary gun.

FIG. 5 is a diagrammatic view of an end component of one embodiment of the diversion device.

FIGS. 6*a*-6*f* are dark field microphotographs illustrating particle densities at the surface, and depths of 35 μm and 50 μm obtained using the inventive capillary gun and the prior art gene gun, respectively.

FIG. 7 are plots of particle penetration depth vs. particle density and vs. distance from the target surface taken from the capillary gun and from the prior art gene gun.

FIG. 8 is a perspective view of a test system of the capillary gun.

DETAILED DESCRIPTION OF THE PREFERRED EMBODIMENTS

Genetic material (DNA, RNA, or plasmids) or dyes can be coated on micron-sized particles and accelerated to high speeds with the use of compressed helium gas (He) resulting in the particles penetrating deep into live tissue or other medium. Without a diversion of the He, the surface of the sample will be damaged by the impact of the gas. The present invention diverts the high speed flow of gas by applying vacuum suction to the gun nozzle in conjunction with the use of thin capillary tubes for the barrel and for the diversion channels. This diversion of the high speed gas prevents the He from impinging on the target surface such that the only damage to the target surface is due to the particles that penetrate into the target.

Figure 2:
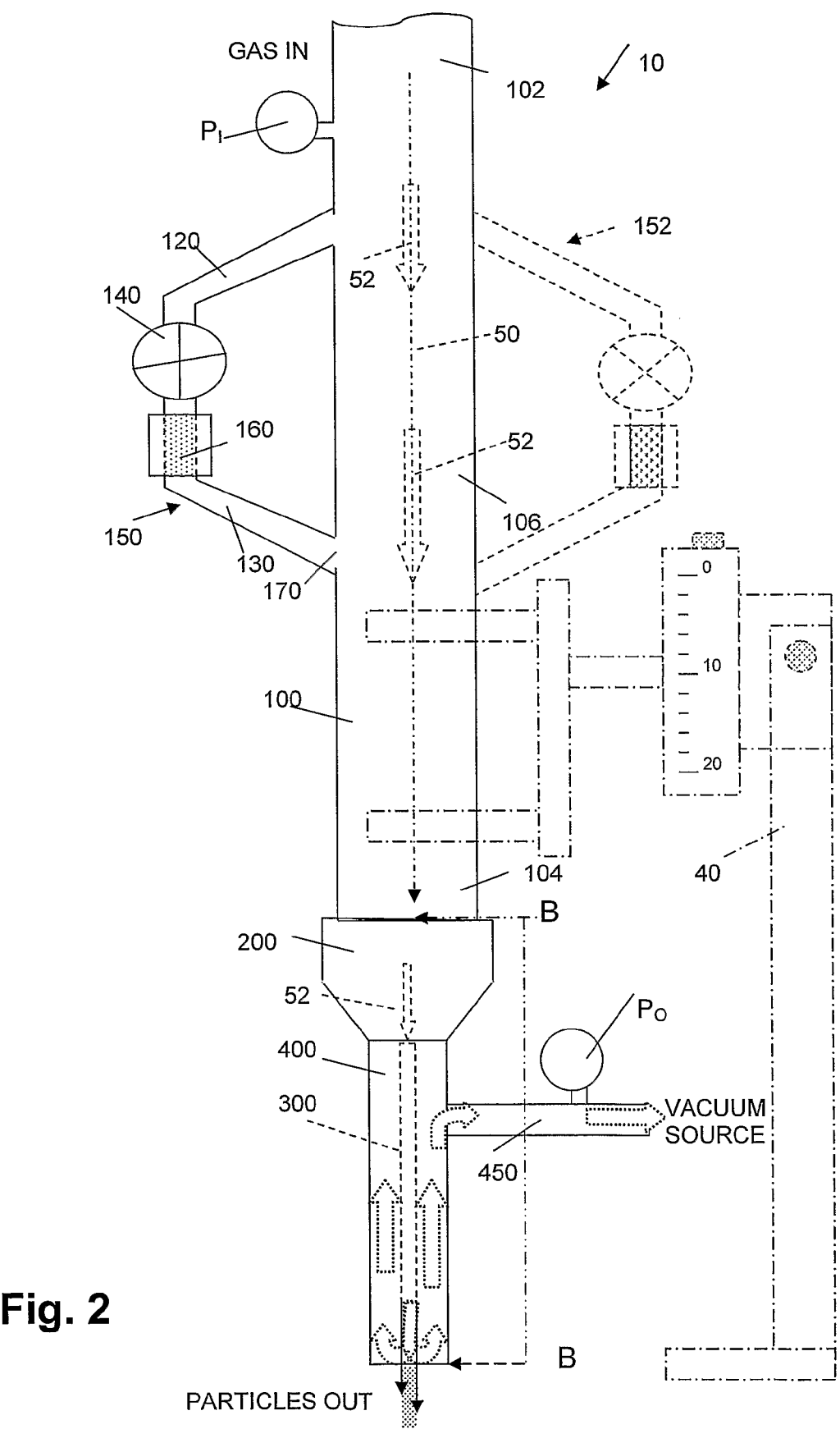
Figure 4:
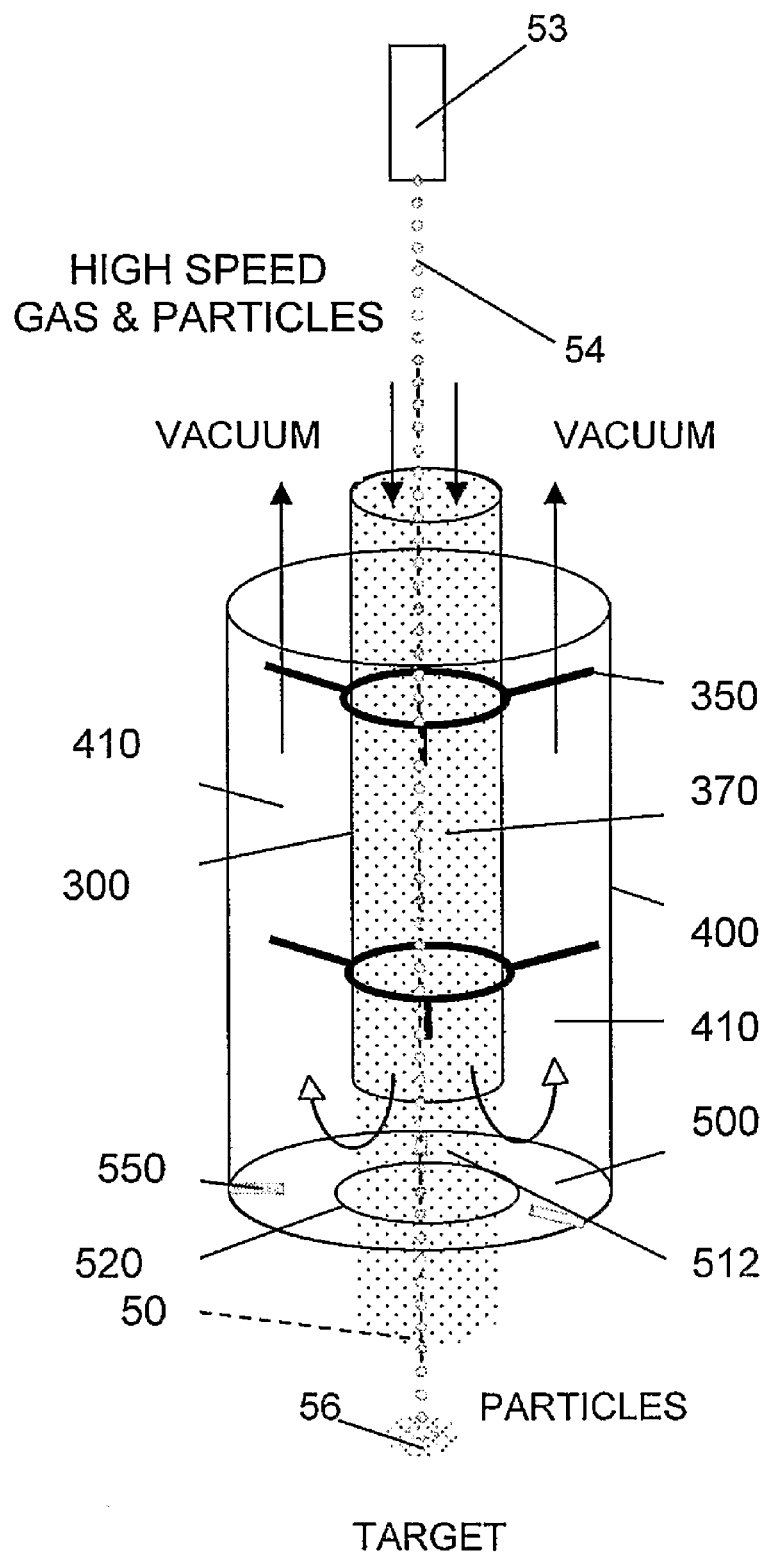

As illustrated in FIGS. 2-4, capillary gun 10 has an proximal section and a distal section. The proximal section is a cylindrical tube 100 having an inlet end 102, a middle section 106, and an outlet end 104. Inlet end 102 is open and is adapted for attachment to a carrier gas source (not shown). In the preferred embodiment, the carrier gas is He. Cylindrical tube 100 may be formed from any appropriate material including stainless steel, brass, copper, or other similar metal, or plastic or polymer. In a prototype system, plastic tubing was used for all lines upstream from the gun, with the connections made using conventional barbed plastic connectors (T- or Y-shaped), plastic stopcocks, and luer connectors.

Attached to the middle section of tube 100 is one or more particle injection loops 150 through which a portion of the gas flow is diverted to carry particles into the gas stream 52. Particle injection loop 150 includes upstream tubing 120 connected at its inlet to tube 100 and at its outlet to the inlet of solenoid valve 140. Solenoid valve 140 controls gas flow into the loop. When valve 140 is opened, gas enters through upstream tube 120, through valve 140 and out through downstream tube 130 back into the primary gas flow stream 52 in tube 100. Particle supply cartridge 160 is positioned downstream from valve 140 so that gas flowing through loop 150 carries particles into flow stream 52. Cartridge 160 is not necessarily a commercially-available container with particles glued inside, as in the Bio-Rad device. Rather, the particles may be loaded as a dry powder into a section of tubing that can be opened and closed. The upstream tubing 120, downstream tubing 130, and cartridge are preferably flexible tubing such as rubber, polypropylene, Tygon®, or other suitable flexible material. The tubing may also be made of stainless steel, brass, copper, or other similar metals with the appropriate fitting for attachment to the tube 100.

A second particle injection loop 152, indicated by dashed lines, may be included to permit the operator to select an alternate type of particles for delivery without disturbing the positioning of the device. Additional injection loops may also be provided for injection of additional kinds of particles.

The above-described particle injection loop configuration is merely one means for injecting particles into the flow stream. It will be readily apparent to those in the art that other particle injection mechanisms may be used for this purpose, and that the invention is not intended to be limited to the described loop.

As illustrated in FIGS. 2 and 9, tube 100 is retained within a clamp 42 or other retaining mechanism that is attached to an adjustable manipulator 40 such as those commercially available from The Micromanipulator Company, Inc. of Carson City, Nev. Manipulator 40 provides multi-axis adjustability (x, y, z and/or rotational axes) which can be used alone or in conjunction with targeting laser 53 (shown in FIGS. 4 and 9 and described below) to permit precise positioning of the device with respect to the target. Note that for ease of illustration, the adjustable manipulator shown in FIG. 8 does not include a base and certain adjustment mechanisms, however, such manipulators are well know to those in the art and the full structure appropriate for this application will be readily apparent.

Outlet end 104 fits closely within the input of plastic luer adapter 200 where it is fixed in place by a appropriate fastening means such as an adhesive, mated threads or other fasteners. Plastic luer adapters are readily commercially available.

The ballistic particles are typically circular in cross-section and may be spherical or cylindrical. Such particles are preferably made of gold or tungsten and are commercially available from Bio-Rad (Hercules, Calif., USA). The particles are approximately 1 μm in diameter.

Luer adapter 200 tapers down and connects at its downstream end to inner capillary tube 300 to direct the gas flow stream and particles into the "barrel" section of the capillary gun. The barrel section end includes inner capillary tube 300, outer capillary tube 400, a plurality of centering pieces 350, end cap 500, and vacuum attachment fitting 450.

Inner capillary tube 300 and outer capillary tube 400 each has a first end and a second end. Inner capillary tube 300 is coaxial with outer capillary tube 400 and is maintained in a centered position by two or more centering pieces 350. Each centering piece 350, illustrated in FIG. 3c, is approximately 150 μm thick and has a spoked configuration with a central ring that fits closely around the outer surface of inner capillary tube 300. The equal length spokes span the space between the outer surface of inner capillary tube 300 and the inner surface of outer tube 400. The spokes are preferably few in number to minimize blockage of vacuum channel 410 while still having sufficient count for stability. As illustrated in FIGS. 3a and 4, there are two centering pieces 350, each having three spokes. Centering pieces 350 are preferably micromachined from UV-curable epoxy based photoresist using contact lithography. One such resist is SU-8™, which available from Micro-Chem of Newton, Mass.

The outer surface of the first end of inner capillary tube 300 is inserted into the downstream end of plastic luer adapter 200 where it is held in place by an appropriate adhesive.

Inner capillary tube 300 may be made from a polyamide-coated fused silica (Micro-Fil™ Gauge 23), which is commercially available from WPI Inc. (Sarasota, Fla., USA). Other appropriate materials include polished glass and plastic with straight smooth walls. The inner diameter ($D_i$) of inner capillary tube 300 may be within a range of 100 μm to 5 mm and is more preferably within the range from 150 μm to 1.6 mm. The length of inner capillary tube 300 may range from 20-30 mm up to 100-150 mm, depending on the diameters of the inner and outer capillary tubes and the application. For example, small diameters would be used for insertion into tight openings, while larger diameters would be used to cover larger areas. In the test system, the inner diameter of the inner capillary tube was approximately 530 μm, the outer diameter was approximately 665 μm and the length from 50 mm to 55 mm.

The first end of outer capillary tube 400 is disposed over the downstream end of plastic luer adapter 200. Outer capillary tube 400 may be formed from plastic or stainless steel tubing having an inner diameter that is large enough to create vacuum channel 410 around inner capillary tube 300. The inner and outer diameters of outer capillary tube 400 will depend on the applications and the dimensions of the inner capillary tube. In the test system, tube 400 an outer diameter of approximately 2.11 mm and an inner diameter of approximately 1.70 mm were used. Appropriate tubing is readily available commercially.

The second end of outer capillary tube 400 is covered by end cap 500, which may be attached with an adhesive. Illustrated in FIG. 3b, end cap 500, also formed from micromachined UV-curable epoxy-based photoresist, is approximately 2.2 mm in diameter and 50 μm thick, with radial support ridges 550 formed on the interior surface to mechanically strengthen the cap and to self center the cap within outer capillary tube 400. Ridges 550 are preferably approximately 100 μm tall with uniform lengths. Orifice 520 is formed in the center of end cap 500 and is coaxially centered within about 25 μm along the flow axis 50. The diameter of orifice 520 can be much smaller than the inner diameter of the inner capillary tube 300, i.e., down to nearly zero (large enough to permit at least one particle to pass through), up to the inner diameter of tube 300. In the test system, orifice 520 had a diameter of approximately 150 µm.

Vacuum orifice 420 is formed through the side of outer capillary tube 400 for attachment of vacuum attachment fitting 450. While shown in the figures at approximately halfway up the length of the tube, it is preferable to locate orifice 420 as close as possible to the second end of tube 400 for improved vacuum efficiency. This must be balanced with other considerations, which include avoiding undue proximity of the suction to the target and minimizing mechanical load on the outer tube that originates from occasional pulling of the vacuum line during use. An external vacuum source (not shown) is connected to vacuum attachment fitting 450 using appropriate tubing (not shown) to create suction within vacuum channel 410. In the test system, vacuum orifice 420 was about 1.5 mm in diameter and was located approximately 20 mm from the second end of outer tube 400.

Figure 8:
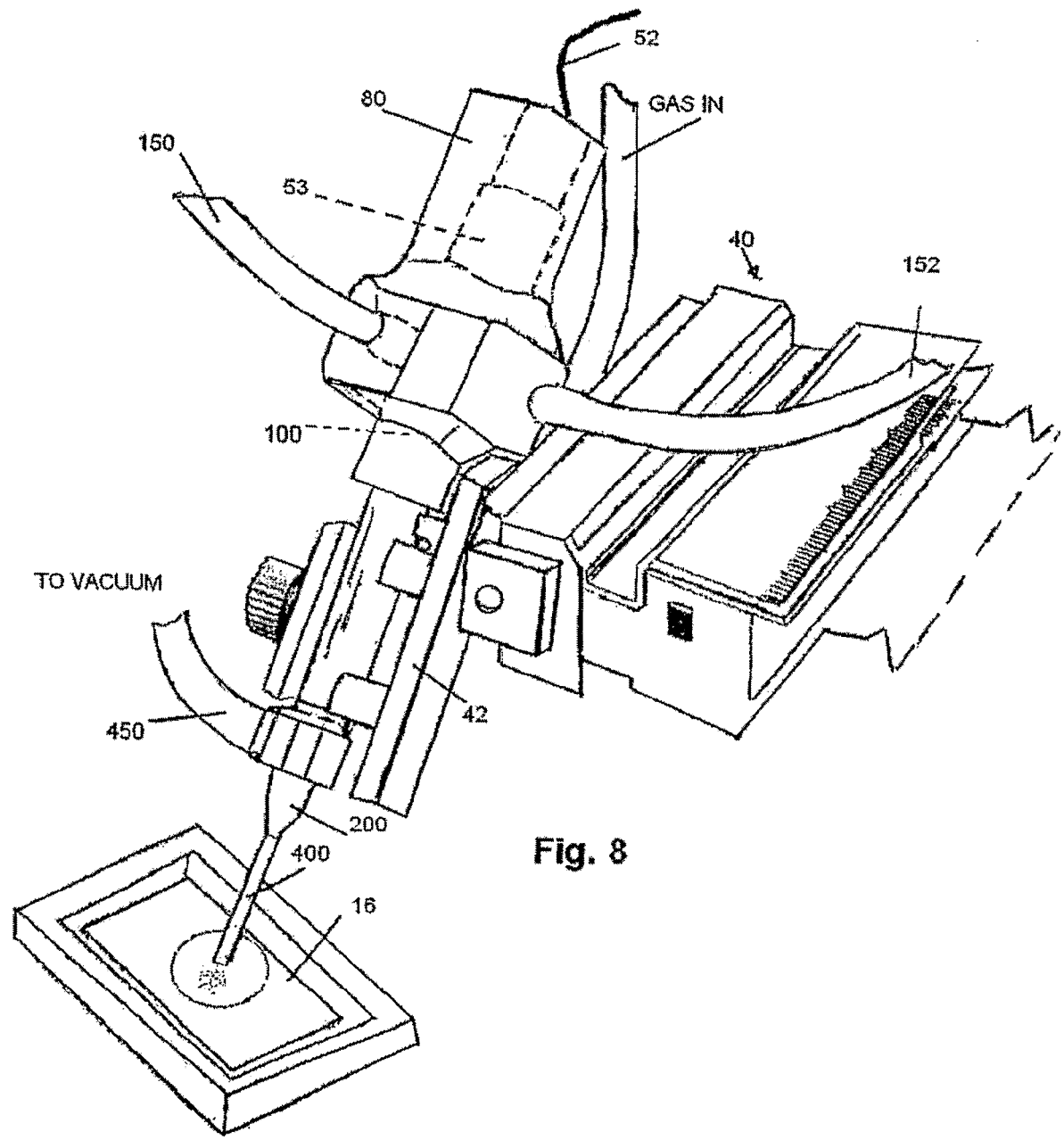

FIGS. 4 and 9 include a diagrammatic illustration of an exemplary laser targeting tool in which visible laser 53 is mounted to direct beam 54 through inner capillary tube 300 coincident with, or very close to flow axis 50. Laser 53 is preferably a semiconductor laser, which facilitates positioning due to its small size, however, adaptation of other types of lasers or light sources will be readily apparent to those in the art. As illustrated in FIG. 8, laser 53 is secured within plexiglass head 80, which is discussed in more detail below in Example 1. Referring again to FIG. 4, beam 54 is focused so that laser spot 56 (exaggerated in size for illustration purposes) illuminates the surface of the target, allowing for optical alignment of the capillary gun with the target. Targeting laser 53 is preferably mounted within tube 100 so that it moves with the capillary gun.

In an alternate embodiment illustrated in FIG. 5, capillary tube 330 has one or more T-connectors 332 (a double T is shown) for attachment of vacuum tubes 430 that draw the gas out of the capillary tube 330 before the particles exit the gun. The T-connected vacuum tubes function in substantially the same manner as the vacuum channel of the first embodiment.

In the preferred embodiment, helium gas is used as the carrier gas. Referring to FIG. 2, the carrier gas is normally continuously flowing through capillary gun 10 through internal channel 180 of tube 100 into and through internal channel 370 of inner capillary tube 300. When the particles are to be added to carrier gas stream 52, solenoid valve 140 is opened. Gas is diverted into upstream tubing 120, forcing the particles from cartridge 160 out of downstream tubing 130 into internal channel 180. Solenoid valve 140 is typically open for about 300 milliseconds. As the particles enter internal channel 180, they are accelerated by the gas flow stream 52 and carried into internal channel 370 of the inner capillary tube 300. The average particle speed will be a fraction of the mean speed of the gas, typically 40-60% or less. The continuous gas flow permits the simultaneous or near-simultaneous addition of different types of particles, i.e., particles having different types of coatings, without disrupting the process or the gas flow. The continuous flow operation also possesses a significant advantage over the prior art by avoiding a pulsed operation that has a greater potential for tissue damage.

As the particles and gas exit the second (outlet) end of inner capillary tube 300, the particles continue in a straight path due to inertia, exiting capillary gun 10 through end cap orifice 520 to impinge upon the target. The suction created in vacuum channel 410 draws gas away from end cap 500. Because this diversion occurs over a distance of less than 1 mm, on a time scale of about 2 µsec, it should have minimal effect on the motion of the particles since they have more inertia than the He gas. To achieve these conditions, the length of outer capillary tube 400 is selected so that spacing 512 between tip 310 of inner capillary tube 300 to inner cap surface 510 is within a range of 0.5 to 3 times the inner diameter of inner capillary tube 300. In the test system, spacing 512 was less than 1 mm. Four different capillary guns were tested having spacings within a range of 600-900 µm. Performance within this range was virtually indistinguishable.

To adjust the gas flow, the vacuum system gauge pressure was measured using a vacuum gauge to find a pressure ($P_o$) of approximately −86 kPa. With the vacuum turned on, tube 100 connected to a He source, and the gas flowing, the flow rate could be adjusted. Capillary gun 10 was held vertically and end cap 500 was placed about 1 mm above the surface of water in a container so that any disturbance in the water by the gas flow would appear as ripples in the water. The He flow, controlled by adjusting the output pressure ($P_i$) from the He source was adjusted upward until ripples were detected in the water. The He pressure was then backed off so there were no ripples in the water surface and was set at 120 kPa, which was about 2-3% below the point at which detectable ripples were generated in the water.

The average speed of the He flow ($\bar{v}_0$) at the outlet of inner capillary tube 300 was measured by placing a gas flow meter (Cole-Palmer, EW-03267-22) upstream from capillary gun 10. The meter was calibrated to display the volumetric flow rate (Q), corresponding to the volume of He at atmospheric pressure, and the $\bar{v}_0$ is calculated as $Q/(\pi D_i^2/4)$ which is approximately 660 m/sec. (With the vacuum suction disconnected and the end cap 500 removed, Q dropped by only 5%, suggesting that the pressure at the outlet of the inner capillary tube 300 was close to atmospheric.) The impact of the flow onto the water surface was less than that of a flow through inner capillary tube 300 at 0.2 m/sec without the vacuum suction Therefore, substantially all of the gas flow was diverted to the vacuum system. Since the density of the tungsten/gold particles is 20 g/cm$^3$, about 10$^5$ times higher than the density of helium (1.7·10$^{-4}$ g/cm$^3$), the momentum required to divert the He flow has negligible impact on the particles.

EXPERIMENTAL

The performance of the inventive capillary gun was characterized and compared to the prior art Helios™ gun. Test shots were made into agarose gels, which are commonly used to emulate live tissues. Three sizes of spherical gold particles from Bio-Rad were used. The sizes were A, B, and C with respective diameters (d), of 0.47±0.15, 1.1±0.1, and 1.27±0.27 µm. The size distribution in the particle samples was characterized using an electron microscope. The gels were inspected under dark-field illumination with a 50×/0.5 objective. Particles will scatter light and look bright under a dark-field illumination. The particles that are in focus appear as small bright dots, while out-of-focus particles contribute to the black background.

Size B particles were shot into a 3% agarose gel and representative photographs are illustrated in FIGS. 6a-6f. FIGS. 6a and 6d are photographs taken at the surface for the inventive capillary gun and the prior art device, respectively. FIGS. 6b and 6e are photographs taken at a depth of 35 µm, and FIGS. 6c and 6f are photographs taken at a depth of 55 µm for the inventive capillary gun and the prior art device, respectively. The distribution produced by the capillary gun show that the particles are spread over an area of approximately 150

μm in diameter, which closely matches the end cap orifice 520 diameter of 150 μm. The distribution produced by the Helios™ gun located approximately 4 cm above the target surface with a He pressure of 175 psi covers an area of about 1.2 cm in diameter.

Figure 7:
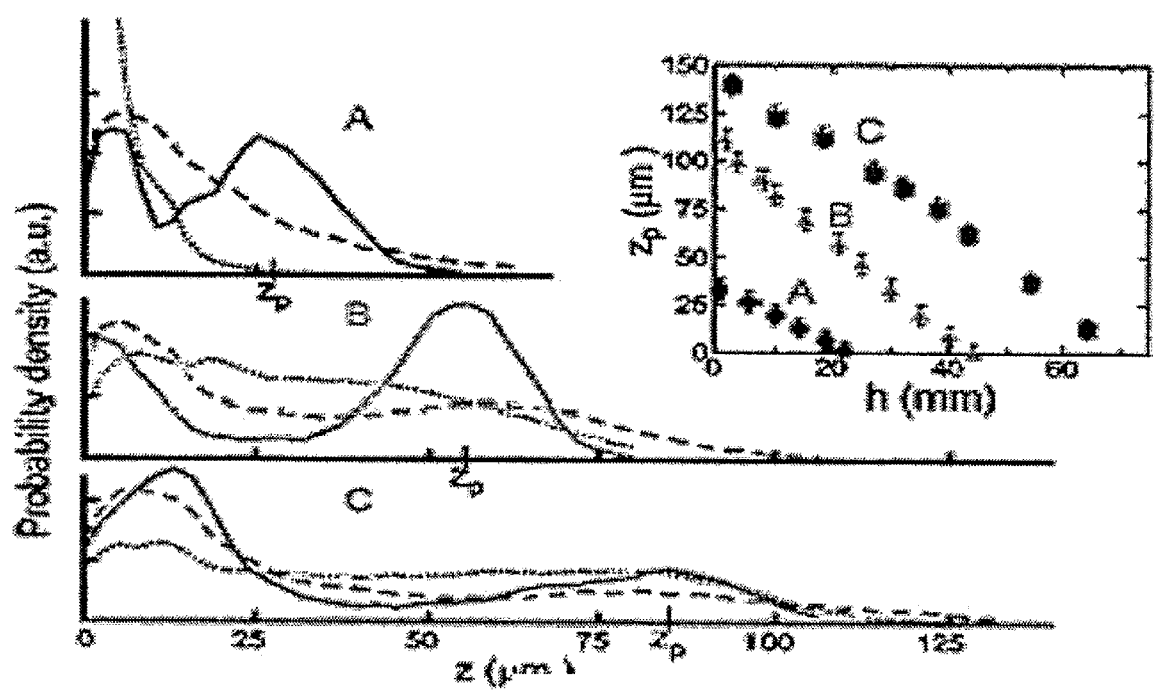

The particle distributions of FIGS. 6a-6f show that the capillary gun delivers very few particles to the surface and a notably larger number of particles to the depth of about 55 μm. In comparison, the prior art gun delivers a significant number of particles to the surface. The graphs in FIG. 7 illustrate the distribution of particle densities for particles A, B, and C at varying depths into the 3% agarose gel for the Helios™ gun and for the capillary gun. The number of particles at the different depths of penetration, z, were counted by taking a stack of images with a step of 3 μm in depth using Image-Pro™ software by Media Cybernetics (Silver Spring, Md., USA) to count the number of bright dots. The Helios™ gun was tested at He gas input pressures of 175 psi and 120 psi. For each of the particles sizes A, B and C, the solid line represents the capillary gun, the dashed line represents the Helios™ gun at an input pressure of 175 psi and the dotted line represents the Helios™ gun at an input pressure of 120 psi. Each curve represents statistics on approximately $10^4$ individual particles.

For the capillary gun, the mean depth of penetration, z, for particles A, B, and C are 20, 39, and 38 μm respectively. For the Helios™ gun, the mean depths of penetration for particles A, B, and C are 17, 36, and 39 μm respectively for the He gas pressure setting of 175 psi, and 4.5, 32, and 48 μm respectively for the He gas pressure setting of 120 psi. The capillary gun has a significant tightening of the particle distribution compared to the Helios™ gun. The capillary gun had the greatest particle density at 55 μm with the B particle. Penetration depths with the capillary gun are consistently larger for small particles, especially when it is important to minimize the impact of the gas jet on the target surface. Further, while the depth distributions for the Helios™ gun are very broad, the distributions for the capillary gun have characteristic peaks at depths $z_p$, near the maximum penetration depths. The peak is the narrowest for the most monodisperse sample B, where about 60% of the particles are found at a z between 40 and 80 μm.

To estimate the velocity of the particles at the maximum peak, $z_p$, shots were made into a 0.25% gel (where the depth of penetration was maximal) in an atmosphere of hydrogen, $H_2$, from various distances, h, between the end cap and the gel surface, and plotted $z_p$ as a function of h (inset in FIG. 7). Hydrogen was chosen because of its high speed of sound ($v_s$ is about 1300 m/sec) and high kinematic viscosity, $\eta_H/\rho_H \approx 1.1 \times 10^{-4}$ m$^2$/s, which reduce nonlinearity in particle flow resistance associated with finite Mach number, $M=u/v_s$, and Reynolds number, $Re=ud\ \rho_H/\eta_H$, respectively. (Here u is the particle velocity). In addition, the viscosity of $H_2$, $\eta_H=9 \times 10^{-6}$ Pa·s, is about half the viscosities of air and He. This expands the range of h and improves resolution of the measurements. The dependencies of $z_p$ on h are close to a linear decay for all three sizes of particles (inset in FIG. 7). The condition $z_p=0$ is met at distances $h_0=22$, 44, and 70 mm for particles A, B, and C, respectively (inset in FIG. 7). The velocity at the peak of the distribution for particles emerging from the gun $u_0$, can be estimated if it is assumed that $z_p=0$ corresponds to $u_p=0$. Assuming that the corrections due to finite M are small, the flow resistance force experienced by the particles can be estimated as $F=-3\pi kd\eta_H u[1+0.15(kRe)^{0.69}]$. Here $k=(1+4.5\ Kn)^{-1}$ is a correction factor for the Stokes resistance due to finite Knudsen number, $Kn=\lambda d$, where $\lambda=0.125$ μm is the mean-free path of the $H_2$ molecules. Using the equation of motion, $F=m\dot{u}=\pi/6d^3\rho_g\dot{u}$, (where $\rho_g=1.93\times10^4$ kg/m$^3$ is the density of gold) to obtain a differential equation for u, and integrate it numerically to obtain $h_0$ as a function of $u_0$ for various d. The values of $u_0$ calculated this way for $h_0$ and mean d of particles A, B, and C are 400, 230, and 280 m/s, respectively, with estimated errors of about 15%. For $H_2$ atmosphere, those values suggest that M<0.3 and less than 1% addition to the resistance due to finite M for all particle sizes, in agreement with the assumption made.

It is instructive to compare the speeds of the particles with characteristic speeds of flow in inner capillary tube 300. The average flow speed at the inner capillary tube outlet is $\bar{v}_0 \approx 660$ m/s, but it is significantly lower upstream from the outlet because of compressibility of helium. At the inner capillary tube inlet, where the absolute pressure is about 2.2 atm, the average speed of He is estimated as $\bar{v}_i = \bar{v}_0/2.2 \approx 290$ m/s. Thus, although the speeds of the particles are significantly lower than $\bar{v}_0$, they are comparable with $\bar{v}_i$. This result appears reasonable in view of large characteristic length, $L_a$, required for acceleration of the particles to the high speeds of flow in the inner capillary tube. The length can be estimated as $L_a \approx v^2/F/m \equiv \rho_g v d^2/18\ k\eta_{He}[1+0.15(kRe)^{0.69}]$. (Here $Re=vd\rho_{He}/\eta_{He}$ with $\rho_{He}=0.165$ kg/m$^3$ and $\eta_{He}=2\cdot10^{-5}$ Pa·s, and k is calculated with $\lambda=0.2$ μm for He molecules.) With $v=\bar{v}_0$, $L_a$ for particles B and C is 55 and 67 mm, respectively, which is comparable to the length of inner capillary tube, $L_i$. For particles A, a relatively short $L_a$ of about 19 mm is obtained, which is a probable reason for their higher characteristic speed.

Increasing $L_i$ while keeping $\bar{v}_0$ the same requires higher driving pressures, which imply proportionally lower $\bar{v}_i$. Thus, guns with longer inner capillary tubes that were tested did not give an appreciable increase in the particle penetration depths. However, the depths significantly increased when $D_i$ was expanded from 250 to 530 μm, allowing lower driving pressure. The expansion of inner capillary tube might also have reduced negative effects of uncontrolled transverse motion of the particles and inelastic collisions with the walls. Those collisions may be a cause of the wide distributions of the particle penetration depths (FIG. 7). Further expansion of the inner capillary tube proved impractical, however, since it caused a reduction of the velocity of the fastest flow which could be diverted to the outer capillary tube.

In an additional experiment, the capillary gun was used to deliver B particles coated with a reporter plasmid expressing green fluorescent protein commercially available from gWIZ; Aldevron (Fargo, N.D., USA) into 293T/17 cells obtained from American Type Culture Collection. After 4 hours, fluorescence from expressed GFP was observed in a number of cells. The capillary gun gives large penetration depths for small particles without damaging the surfaces of even the most delicate targets (0.25% agarose gels). It selectively targets small areas and can be inserted into openings down to 2.5 mm in size.

The capillary gun may be used in applications in medicine and live animal biology. A large fraction of the particles is delivered to a narrow interval of depths, and the characteristic penetration depth is reliably controlled by tailoring the shooting distance. The device can target very small areas of a few 100×100 μm$^2$. The ability to estimate and control the speed of the particles makes the gun a promising tool for studying microscopic mechanical properties of soft materials. In addition to firing small spherical particles, the device can also fire thin (12.5-25 μm diameter) pieces of wire that can be used as electrodes.

An important improvement provided by the present invention is that a "shot" of particles is made not by generating a pulse of gas flow, but rather by injection of particles into a continuous flow of gas in the barrel. The continuous gas flow changes very little between an idle run and a shot. It is this features that allows concurrent injection of different types of particles into the same flow, with injection of each type of particle being individually controlled. The continuous gas flow also allows injection of small (potentially, arbitrarily small) amounts of particles at a high rate, which provides the ability to digitally quantify the injection of particles (and chemicals).

The following example provides an exemplary application of the inventive capillary gun and method for implantation of genetic materials. The example is not intended to be limiting, and the device and method may be used for other applications as previously described.

Example 1

Localized Delivery of dsRNA and Plasmid DNA into Leech Embryos

The inventive capillary gun was used for localized delivery of dsRNA and plasmid DNA into muscle cells and central neurons of live embryos of the medical leech, *Hirudo medicinalis*. The leech embryo is a useful model for studying the influence of expression levels of specific genes on the morphology and function of the nervous system.

Referring to FIG. 8, to adapt the gun for accurate delivery of particles into the embryos, it was mounted on a micromanipulator 40, and a specially designed head 80 was attached to the gun. Head 80 was machined of Plexiglas®, with its upper part adapted to retain semiconductor laser 53 with an adjustable lens (not shown). Laser 53 generates a beam of light directed through the inner capillary, focused at the embryo surface in sample stage 16 (a few mm from the nozzle) and used for aiming. The surface of the embryo was imaged with a video microscope (magnification 0.7-4.5×) (not shown). The lower part of head 80 had a He outlet at the bottom, connected to the gun through a luer adapter, and three inlets on the sides that were all connected to the same source of pressurized He through separate lines of tygon tubing. One line (labeled "Gas In") was always open, creating a continuous flow of He through the gun. Two other lines 150 and 152 were normally closed by solenoid valves and contained gold carrier particles (1.6 μm in diameter) with different coatings that were loaded into the tubing as a dry powder. A shot was generated by opening one of the valves for 0.3 s, causing the injection of a bolus of particles from the corresponding tubing line into the gun. One load of particles weighed about 0.5 mg and could typically be used for up to ten shots, with a single shot usually delivering on the order of a few hundred particles. The tubing was gently tapped between the shots to dislodge particles and facilitate their injection into the He stream in the gun.

The outer capillary of the gun was connected to a vacuum system with a gauge pressure of −12.5 psi. The pressure of He was varied between 10 and 15 psi to adjust the particle penetration depth. The upper pressure limit was set by a level at which a jet of He started to emerge from the gun nozzle. Distributions of penetration depths of the particles into leech embryos were similar to the distributions obtained with agarose gels. Importantly, at all He pressures tested, the distributions had a single peak, and the particles were localized in a narrow interval of depths around the peak (width at half height of ~15 μm).

It was demonstrated (Shefi et al., to be published) that silencing of expression of the axon guidance factor netrin could be achieved by RNA interference (RNAi) using the capillary gun for local delivery of dsRNA. The gun was also used to induce ectopic expression of an EGFP-tagged actin, in small clusters of longitudinal muscle cells and central neurons. In addition, an independent injection of two different fluorescent dyes into a leech embryo in a single assay was demonstrated.

As a method for RNAi and transfection of cells in a localized region of a tissue, the biolistic delivery of nucleic acids with the gun has several advantages over microcapillary injection and electroporation: it is fast, contact-free and non-destructive. Unlike localized electroporation, delivery of substances with the gun has little sensitivity to specific properties of the cells and tissue other than their mechanical strength. The gun targets multiple cells at once, while microcapillary injection into multiple neighboring cells would normally be impractical because of the high probability of damage to the cells from the introduction and removal of the capillary tip. A unique feature of the gun is the possibility of independent injection of different substances, with no unwanted intermixing between them and a minimal time required to inject an additional substance. The volume of the tissue affected by a single shot can be easily adjusted by varying the diameter of the gun nozzle and the distribution of particle sizes. It is anticipated that with an appropriate reduction of the nozzle diameter, the size of the particle delivery region can be reduced to diameter of a single cell (~15 μm).

The specific RNAi-mediated silencing of the expression of the axon guidance factor netrin during embryonic development that is achieved with the gun allows practically non-invasive microscopic-level control of axonal growth. Since the localized netrin silencing assay is fast and non-destructive, it could be applied at multiple spots of an embryo, allowing a pre-designed pattern of innervation cues to be inscribed in an embryo. Furthermore, by using particles with different coatings stored in separate reservoirs and independently injected into the He flow, different sets of dsRNA and plasmid DNA can be delivered to specified regions of a tissue, leading to expression or inhibition of different combinations of genes. If programmable positioning and motion of the gun along with higher resolution microscopy and better control of particle injection into the He flow are implemented, we expect that concurrent manipulation of expression of multiple genes according to a pre-designed spatial pattern can be achieved using the gun.

PUBLISHED REFERENCES (INCORPORATED HEREIN BY REFERENCE)

Aisemberg G O, Gershon T R, Macagno E R (1997), "New electrical properties of neurons induced by a homeoprotein", *Journal of Neurobiology* 33: 11-17.

Baker M W, Macagno E R (2000), "RNAi of the receptor tyrosine phosphatase HmLAR2 in a single cell of an intact leech embryo leads to growth-cone collapse", *Current Biology* 10: 1071-1074.

Biswas S C, Dutt A, Baker M W, Macagno E R (2002), "Association of LAR-like receptor protein tyrosine phosphatases with an enabled homolog in Hirudo medicinalis", *Molecular and Cellular Neuroscience* 21: 657-670.

Gan W B, Grutzendler J, Wong W T, Wong R O L, Lichtnan J W (2000), "Multicolor "DiOlistic" labeling of the nervous system using lipophilic dye combinations", *Neuron* 27: 219-225.

Hammond S M, Caudy A A, Hannon G J (2001), "Post-transcriptional gene silencing by double-stranded RNA", *Nature Reviews Genetics* 2: 110-119.

Hon H, Rucker E B, Hennighausen L, Jacob J (2004), "bcl-X-L is critical for dendritic cell survival in vivo", *Journal of Immunology* 173: 4425-4432.

Kim T W, Lee J H, He L M, Boyd D A K, Hardwick J M, Hung C F, Wu T C (2005), "Modification of professional antigen-presenting cells with small interfering RNA in vivo to enhance cancer vaccine potency", *Cancer Research* 65: 309-316.

Klein T M, Wolf E D, Wu R, Sanford J C (1987), "High-Velocity Microprojectiles for Delivering Nucleic-Acids Into Living Cells," *Nature* 327: 70-73.

Mehier-Humbert S, Guy R H (2005), "Physical methods for gene transfer: Improving the kinetics of gene delivery into cells", *Advanced Drug Delivery Reviews* 57: 733-753.

Rinberg D, Simonnet C, Groisman A (2005), "Pneumatic capillary gun for ballistic delivery of microparticles", *Applied Physics Letters* 87, 014103.

Shefi 0, Simonnet C, Baker M W, Glass J R, Macagno E R, Groisman A, "Microtargeted gene silencing and ectopic expression in live embryos using biolistic delivery with a pneumatic capillary gun", (Submitted for publication in *Nature Neuroscience*, manuscript #NN-T17118.)

Thorey I S, Zipser B (1991), "The Segmentation of the Leech Nervous-System Is Prefigured by Myogenic Cells at the Embryonic Midline Expressing A Muscle-Specific Matrix Protein", *Journal of Neuroscience* 11: 1786-1799.

Wang W Z, Emes R D, Christoffers K, Verrall J, Blackshaw S E (2005), Hirudo medicinalis: A platform for investigating genes in neural repair", *Cellular and Molecular Neurobiology* 25: 427-440.

What is claimed is:

1. A capillary gun for delivery of ballistic particles into a target, the gun comprising:
   a flow tube connected to a gas source for directing a carrier gas stream along a flow axis, wherein the carrier gas stream has a flow rate for accelerating the particles to a delivery velocity;
   a capillary tube having an inner diameter, an outer diameter, and a tube axis coaxial with the flow axis for receiving the particles and carrier gas from the flow tube and directing the particles and carrier gas toward the target, the capillary tube having an outlet end;
   a plurality of particle injectors connected to at least one of the flow tube and the capillary tube for introducing particles into the carrier gas stream to be carried through the capillary tube along the flow axis, wherein each particle injector of the plurality is adapted to inject a different particle type;
   a suction channel disposed near the outlet end of the capillary tube for-diverting the carrier gas from the flow axis so that the particles continue along the flow axis at the delivery velocity to impinge upon the target located at a distance from the outlet end of the capillary tube; and
   a vacuum source for applying the suction to the vacuum channel.

2. The capillary gun of claim 1, wherein the suction channel is defined by a vacuum tube having an inner diameter larger than the outer diameter of the capillary tube and disposed coaxially with the capillary tube, wherein a distal end of the vacuum tube extends slightly beyond the outlet end of the capillary tube so that the gas is drawn into the vacuum tube as the gas and particles exit the outlet end of the capillary tube.

3. The capillary gun of claim 2, further comprising an end cap disposed on the distal end of the vacuum tube, the end cap having an orifice therethrough to permit the particles to continue along the flow axis.

4. The capillary gun of claim 3, wherein a spacing between the outlet end of the capillary tube and an inner surface of the end cap is within a range of 0.5 to 3 times the inner diameter of the capillary tube.

5. The capillary gun of claim 3, wherein the orifice has a diameter within a range of much smaller than the inner diameter up to the inner diameter of the capillary tube.

6. The capillary gun of claim 2, wherein substantially all gas flow emerging from the outlet end of the capillary tube is diverted into the suction channel.

7. The capillary gun of claim 2, further comprising a plurality of centering pieces for maintaining a uniform space between the capillary tube and the vacuum tube and for centering the capillary tube within the vacuum tube.

8. The capillary gun of claim 1, wherein the capillary tube has an inner diameter within the range of 100 µm to 5 mm.

9. The capillary gun of claim 1, wherein the different particle type within each particle injector comprises a plurality of particles having a molecular coating different from molecular coatings of particles within other particle injectors.

10. The capillary gun of claim 1, wherein the different particle type have coatings selected from the group consisting of DNA, RNA, dyes and drugs.

11. The capillary gun of claim 1, further comprising a laser disposed within or on the capillary gun for directing a visible targeting beam along the flow axis to illuminate a targeted area.

12. The capillary gun of claim 1, further comprising an adjustable manipulator for releasably retaining and controlling positioning of the capillary gun.

13. The capillary gun of claim 1, wherein the capillary gun is one of an array of capillary guns for delivering particles to multiple targets.

14. A method for launching microscopic particles into a target, comprising:
   directing a carrier gas flow through a flow tube along a flow axis;
   injecting particles into the carrier gas flow from a plurality of particle injectors so that the particles are accelerated to a delivery velocity, wherein each particle injector of the plurality is adapted to inject a different particle type;
   directing the carrier gas flow and particles into a capillary tube having a tube axis coaxial with the flow axis at a downstream end of the flow tube;
   diverting substantially all of the carrier gas flow from the flow axis near an outlet end of the capillary tube by applying a suction near the outlet end so that the particles continue along the flow axis out of the capillary tube at the delivery velocity to impinge upon the target at a distance from the outlet end of the capillary tube.

15. The method of claim 14, wherein the gas flow is continuous and is continuously diverted from the outlet end of the capillary tube.

16. The method of claim 14, wherein the suction is applied by a suction channel defined by a vacuum tube having an inner diameter larger than the outer diameter of the capillary tube and disposed coaxially with the capillary tube, wherein a distal end of the vacuum tube extends slightly beyond a distal end of the capillary tube so that the gas is drawn into the vacuum tube as the gas and particles exit the outlet end of the capillary tube.

17. The method of claim 14, further comprising disposing an end cap on the distal end of the vacuum tube, wherein the end cap has an orifice therethrough to permit the particles to continue along the flow axis.

18. The method of claim 17, wherein a spacing between the outlet end of the capillary tube and an inner surface of the end cap is within a range of 0.5 to 3 times the inner diameter of the capillary tube.

19. The method of claim 17, wherein the orifice has a diameter within a range of much smaller than the inner diameter up to the inner diameter of the capillary tube.

20. The method of claim 14, wherein the capillary tube has an inner diameter within the range of 100 μm to 5 mm.

21. The capillary gun of claim 14, wherein the different particle types have coatings selected from the group consisting of DNA, RNA, dyes and drugs.

22. The method of claim 14, further comprising disposing a laser within or on the capillary gun for directing a visible targeting beam along the flow axis to illuminate a targeted area.

23. The method of claim 14, further comprising supporting the capillary gun on an adjustable manipulator for controlling positioning of the capillary gun.

24. A capillary gun for delivery of ballistic particles into a target, the gun comprising:
- a capillary tube having a tube axis defining a flow axis and an outlet end having an orifice disposed within the flow axis;
- a flow tube connected at a first end to a gas source and at a second end to the capillary tube for directing a carrier gas stream along the flow axis;
- at least one particle loop in fluid communication with the flow tube for introducing particles into the carrier gas stream for acceleration to a delivery velocity;
- a suction channel disposed near the outlet end of the capillary tube for diverting substantially all the carrier gas from the flow axis so that the particles pass through the orifice at a delivery velocity to impinge upon the target at a distance from the outlet end of the capillary tube; and
- a vacuum source for applying the suction to the vacuum channel.

25. The capillary gun of claim 24, wherein the suction channel is defined by a vacuum tube having an inner diameter larger than the outer diameter of the capillary tube and disposed coaxially with the capillary tube, wherein a distal end of the vacuum tube extends slightly beyond the outlet end of the capillary tube so that the gas is drawn into the vacuum tube as the gas and particles exit the outlet end of the capillary tube.

26. The capillary gun of claim 24, wherein the orifice has a diameter within a range of much smaller than an inner diameter of the capillary tube up to the inner diameter of the capillary tube.

27. The capillary gun of claim 24, wherein the capillary tube has an inner diameter within the range of 100 μm to 5 mm.

28. The capillary gun of claim 24, wherein the at least one particle injection loop comprises a plurality of particle injectors, wherein each particle injector of the plurality is adapted to inject a different particle type.

29. The capillary gun of claim 28, wherein the different particle type within each particle injector comprises a plurality of particles having a molecular coating different from molecular coatings of particles within other particle injectors.

30. The capillary gun of claim 28, wherein the different particle types have coatings selected from the group consisting of DNA, RNA, dyes and drugs.

31. The capillary gun of claim 24, further comprising a laser disposed within or on the capillary gun for directing a visible targeting beam along the flow axis to illuminate a targeted area.

32. The capillary gun of claim 24, further comprising an adjustable manipulator for releasably retaining and controlling positioning of the capillary gun.

33. The capillary gun of claim 24, wherein the capillary gun is one of an array of capillary guns for delivering particles to multiple targets.

* * * * *